United States Patent

Stähle et al.

[11] 4,250,186
[45] Feb. 10, 1981

[54] METHOD OF SLOWING HEART RATE

[75] Inventors: Helmut Stähle; Herbert Köppe; Werner Kummer, all of Ingelheim am Rhein; Wolfgang Hoefke, Budenheim; Wolfram Gaida, Ingelheim am Rhein, all of Fed. Rep. of Germany; Ludwig Pichler, Vienna, Austria

[73] Assignee: Boehringer Ingelheim GmbH, Ingelheim am Rhein, Fed. Rep. of Germany

[21] Appl. No.: 12,650

[22] Filed: Feb. 16, 1979

[30] Foreign Application Priority Data

Feb. 17, 1978 [DE] Fed. Rep. of Germany ....... 2806775

[51] Int. Cl.$^3$ ............................................ A61K 31/415
[52] U.S. Cl. ................................ 424/273 R; 548/315
[58] Field of Search ...................... 548/315; 424/273 R

[56] References Cited

U.S. PATENT DOCUMENTS

| | | | |
|---|---|---|---|
| 2,899,426 | 8/1959 | Bloom | 548/315 |
| 2,938,038 | 5/1960 | Hirt | 548/315 |
| 3,468,887 | 9/1969 | Stähle et al. | 548/315 |
| 3,595,961 | 7/1971 | Stähle et al. | 548/315 |
| 4,025,607 | 5/1977 | Stähle et al. | 548/315 |

OTHER PUBLICATIONS

Conant et al., The Chemistry of Organic Compounds 3rd Ed., p. 342, N. Y., MacMillan, 1947.

Primary Examiner—Henry R. Jiles
Assistant Examiner—R. W. Ramsuer
Attorney, Agent, or Firm—Hammond & Littell, Weissenberger & Muserlian

[57] ABSTRACT

Compounds of the formula

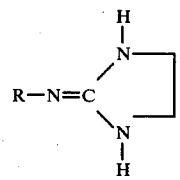

wherein

R is 2-bromo-4,5-dihydroxy-phenyl; 3-chloro-4-hydroxy-phenyl; 4-bromo-2,5-dihydroxy-phenyl; 3,5-dihydroxy-phenyl; 5-chloro-2,4-dihydroxy-phenyl; 3-hydroxy-4-methyl-phenyl; 2,6-dibromo-4-hydroxymethyl-phenyl; 3,5-dibromo-4-aminophenyl; 3-methylmercapto-phenyl; 3,4,5-trihydroxy-phenyl; or 3-bromo-4-fluoro-phenyl;

and non-toxic, pharmacologically acceptable acid addition salts thereof. The compounds as well as their salts are useful as bradycardiacs.

1 Claim, No Drawings

METHOD OF SLOWING HEART RATE

This invention relates to novel 2-phenylaminoimidazolidines and acid addition salts thereof, as well as to methods of preparing these compounds, pharmaceutical compositions containing them as active ingredients, and methods of using them as bradycardiacs.

THE PRIOR ART

Because of their outstanding pharmacological and therapeutic properties, 2-phenylimino-imidazolidines have for a long time commanded strong interest in the pharmaceutical industry. Therefore, compounds of this type have often been reported in the literature and are disclosed, for example in Belgian Pat. Nos. 623,305; 653,933; 687,656; 687,657; and 705,944. These prior disclosures also describe the principal methods for the preparation of 2-phenylimino-imidazolidines.

More particularly, the present invention relates to a novel group of 2-(substituted phenyl-imino)-imidazolidines represented by the formula

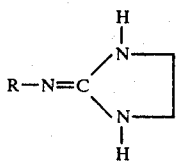

wherein R
is 2-bromo-4,5-dihydroxy-phenyl; 3-chloro-4-hydroxy-phenyl; 4-bromo-2,5-dihydroxy-phenyl; 3,5-dihydroxy-phenyl; 5-chloro-2,4-dihydroxy-phenyl; 3-hydroxy-4-methyl-phenyl; 2,6-dibromo-4-hydroxy-methyl-phenyl; 3,5-dibromo-4-aminophenyl; 3-methyl-mercapto-phenyl; 3,4,5-trihydroxy-phenyl; or 3-bromo-4-fluoro-phenyl;
and non-toxic, pharmacologically acceptable acid addition salts thereof.

The compounds embraced by formula I may be prepared by the following methods:

Method A.

By reacting a compound of the formula

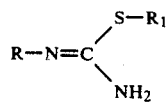

wherein R has the same meanings as in formula I, and $R_1$ is hydrogen or alkyl of 1 to 4 carbon atoms, or an acid addition salt thereof, with ethylenediamine or an acid addition salt thereof.

The reaction is performed at temperatures between 0° and 200° C., with or without a solvent. Polar protic, polar aprotic or non-polar solvents may be used. If the reaction is performed without a solvent, elevated temperatures should be applied. The reaction time depends upon the reactivity of the reactants and varies between a few minutes and several hours.

Method B

For the preparation of those compounds of the formula I where R is hydroxyl-substituted phenyl, by ether cleavage of a compound of the formula

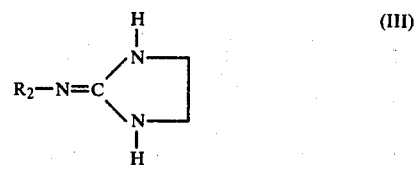

wherein
$R_2$ is 2-bromo-4,5-dimethoxy-phenyl; 3-chloro-4-methoxy-phenyl; 4-bromo-2,5-dimethoxy-phenyl; 3,5-dimethoxy-phenyl; 5-chloro-2,4-dimethoxy-phenyl; 3-methoxy-4-methyl-phenyl; or 3,4,5-trimethoxy-phenyl;
with a strong acid.

The ether cleavage is most advantageously performed with concentrated hydrobromic acid at elevated temperatures. However, it may also be effected with the aid of a Lewis acid under conditions which are known from the literature.

The starting compounds of the formula II may be obtained by converting a corresponding aniline with isocyanate into the analogous isothiourea, converting the latter with an alkylating agent into an isothiouronium salt, and treating this acid addition compound with a base to form the desired isothiourea compound.

The starting compounds of the formula III may be obtained by reacting an isothiourea of the formula

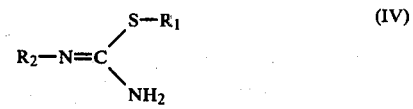

wherein $R_1$ and $R_2$ have the meanings previously defined, or an acid addition salt thereof, with ethylenediamine or an acid addition salt thereof.

The compounds embraced by formula I above are organic bases and therefore form addition salts with inorganic or organic acids. Examples of non-toxic, pharmacologically acceptable acid addition salts are those formed with hydrochloric acid, hydrobromic acid, hydroiodic acid, hydrofluoric acid, sulfuric acid, phosphoric acid, nitric acid, acetic acid, propionic acid, butyric acid, caproic acid, valeric acid, oxalic acid, malonic acid, succinic acid, maleic acid, fumaric acid, lactic acid, tartaric acid, citric acid, malic acid, benzoic acid, p-hydroxybenzoic acid, p-aminobenzoic acid, phthalic acid, cinnamic acid, salicylic acid, ascorbic acid, methanesulfonic acid, 8-chlorotheophylline or the like.

The following examples illustrate the present invention and will enable others skilled in the art to understand it more completely. It should be understood, however, that the invention is not limited solely to the particular examples given below.

EXAMPLE 1

2-(2-Bromo-4,5-dihydroxy-phenylimino)-imidazolidine hydrobromide by method B

A mixture of 3.60 gm of 2-(2-bromo-4,5-dimethoxy-phenylimino)-imidazolidine base (0.012 mol) and 100 ml of 48% hydrobromic acid was refluxed on an oil bath for eight hours while stirring. Thereafter, the hydrobromic acid was evaporated in vacuo, and the residue was dissolved in methanol. The resulting solution was purified by treatment with activated charcoal and filtration, and ether was added to the filtrate. A white crystalline substance precipitated, which was collected and dried, yielding 2.95 gm (90.35% of theory) on the compound of the formula

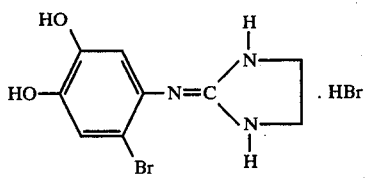

which had a melting point of 203°-205° C. and an $R_f$-value of 0.4 in a mobile phase consisting of 75 parts sec.butanol, 15 parts formic acid and 10 parts water. Carrier: Silicagel; visualization: potassium iodoplatinate.

The starting compound was prepared by brominating 2-(3,4-dimethoxy-phenylimino)-imidazolidine.

EXAMPLE 2

2-(3-Chloro-4-hydroxy-phenylimino)-imidazolidine hydrobromide by method B

A mixture of 8 gm of 2-(3-chloro-4-methoxy-phenylimino)-imidazolidine hydrobromide (0.026 mol) and 125 ml of 48% hydrobromic acid was refluxed on an oil bath for five hours. Thereafter, the hydrobromic acid was evaporated in vacuo, the residue was dissolved in methanol, and the solution was purified by treatment with activated charcoal and filtration. Ether was added to the filtrate, whereby an amorphous product separated out which was collected and dried, yielding 5.60 gm (73.6% of theory) of 2-(3-chloro-4-hydroxy-phenylimino)-imidazolidine hydrobromide, m.p. 224°-225° C., $R_f$-value 0.4 in mobile phase consisting of 75 parts sec.butanol, 15 parts formic acid and 10 parts water. Carrier: Silicagel; visualization: ultraviolet light and potassium iodoplatinate.

The starting compound was prepared by converting 3-chloro-4-methoxy-aniline into the corresponding isothiouronium salt and reacting the latter with ethylenediamine.

EXAMPLE 3

2-(4-Bromo-2,5-dihydroxy-phenylimino)-imidazolidine hydrobromide by method B

A mixture of 6 gm of 2-(4-bromo-2,5-dimethoxy-phenylimino)-imidazolidine hydrobromide (0.0157 mol) and 100 ml of 48% hydrobromic acid was refluxed for 6 hours on an oil bath. Thereafter, the clear, homogeneous reaction mixture was allowed to stand in the refrigerator overnight, and the crystalline precipitate formed thereby was collected by suction filtration, washed with ether and dried. Yield: 0.95 gm (17.15% of theory) of 2-(4-bromo-2,5-dihydroxy-phenylimino)-imidazolidine hydrobromide, m.p. 219°-220° C., $R_f$-value 0.5 in the mobile phase 75 parts sec.butanol, 15 parts formic acid, 10 parts water. Carrier: Silicagel; visualization: potassium iodoplatinate.

The starting compound was prepared by brominating 2-(2,5-dimethoxy-phenylimino)-imidazolidine.

EXAMPLE 4

2-(3,5-Dihydroxy-phenylimino)-imidazolidine hydrobromide by method B

A mixture of 6.05 gm of 2-(3,5-dimethoxy-phenylimino)-imidazolidine hydrobromide (0.02 mol) and 100 ml of 48% hydrobromic acid was refluxed for 2½ hours while stirring. Thereafter, the hydrobromic acid was evaporated in vacuo, ether was stirred into the residue, the precipitate formed thereby was collected by suction filtration, and the filter cake was washed with ether and dried. Yield: 4.9 gm (89.37% of theory) of 2-(3,5-dihydroxy-phenylimino)-imidazolidine hydrobromide, m.p. 127°-128° C., $R_f$-value 0.5 in mobile phase 75 parts sec.butanol, 15 parts formic acid, 10 parts water. Carrier: silicagel with fluorescent pigment ZS; visualization: ultraviolet light and potassium iodoplatinate.

The starting compound was prepared by reacting 3,5-dimethoxy-aniline with ammonium thiocyanate, methylating the reaction product to form the corresponding S-methyl-isothiouronium salt, and subjecting the latter to condensation with ethylenediamine.

EXAMPLE 5

2-(5-Chloro-2,4-dihydroxy-phenylimino)-imidazolidine hydrobromide by method B

A mixture of 10 gm of 2-(5-chloro-2,4-dimethoxy-phenylimino)-imidazolidine (0.03 mol) and 150 ml of 48% hydrobromic acid was refluxed for six hours. Thereafter, the clear, homogeneous reaction mixture was allowed to stand overnight in the refrigerator. The crystalline precipitate which had formed was collected by suction filtration, washed with ether and dried, yielding 5.6 gm (60.5% of theory) of 2-(5-chloro-2,4-dihydroxy-phenylimino)-imidazolidine hydrobromide, $R_f$-value 0.5 in mobile phase 75 parts sec.butanol, 15 parts formic acid, 10 parts water. Carrier: silicagel; visualization: potassium iodoplatinate.

The starting compound was prepared by reacting N-(5-chloro-2,4-dimethoxy-phenyl)-S-methyl-isothiouronium iodide with ethylenediamine.

EXAMPLE 6

2-(3-Hydroxy-4-methyl-phenylimino)-imidazolidine hydrobromide by method B

A mixture of 6.61 gm of 2-(3-methoxy-4-methyl-phenylimino)-imidazolidine base (0.032 mol) and 100 ml of 48% hydrobromic acid was refluxed for 12 hours while stirring. Thereafter, the hydrobromic acid was evaporated in value, the residue was dissolved in methanol, the solution was filtered, and ether was added to the filtrate. The crystalline precipitate formed thereby was collected by suction filtration, washed with ether and dried. Yield: 4.85 gm (55.65% of theory) of 2-(3-hydroxy-4-methyl-phenylimino)-imidazolidine hydrobromide, m.p. 164°-165° C., $R_f$-value 0.4 in mobile phase 75 parts sec. butanol, 15 parts formic acid, 10 parts water. Carrier: silicagel with fluorescent pigment

EXAMPLE 7

2-(2,6-Dibromo-4-hydroxymethyl-phenylimino)-imidazolidine hydrochloride by method A A mixture of 35.5 gm (0.0735 mol) of 2-(2,6-di-bromo-4-hydroxymethyl-phenyl)-S-methyl-isothiouronium iodide, 7.5 ml of ethylenediamine and 75 ml of butanol was refluxed for eight hours. Thereafter, the solvent was evaporated in vacuo, the residue was dissolved in 2 N hydrochloric acid, and the solution was extracted with ether. The ethereal extracts were discarded. The aqueous phase was made stepwise alkaline with 2 N sodium hydroxide and was then fractionally extracted with ethyl acetate. The uniform fractions were evaporated in vacuo, the residue was dissolved in methanol, the solution was made acid to Congo red with hydrochloric acid, and the resulting clear solution was admixed with ether. The amorphous precipitate was collected by suction filtration, washed with ether and dried. Yield: 1.60 gm (5.60% of theory of 2-(2,6-dibromo-4-hydroxymethyl-phenylimino)-imidazolidine hydrochloride, m.p. 267°–268° C., $R_f$-value 0.6 in mobile phase 50 parts benzene, 50 parts dioxane, 5 parts ethanol, 5 parts concentrated aqueous ammonium hydroxide. Carrier: silicagel; visualization: potassium iodoplatinate.

The starting compound was prepared by bromination of methyl 4-amino-benzoate, followed by reduction of the intermediate with lithium aluminum hydride.

EXAMPLE 8

2-(4-Amino-3,5-dibromo-phenylimino)-imidazolidine hydrochloride by method A

A mixture of 30.35 gm (0.065 mol) of 2-(4-amino-3,5-dibromo-phenyl)-S-methyl-isothiouronium hydroiodide, 6.5 mol of ethylenediamine and 65 ml of methanol was refluxed for 10 hours. Thereafter, the methanol was evaporated in vacuo, and the viscous residue was dissolved in methanol. The solution was filtered, and the filtrate was made alkaline with aqueous 50% potassium hydroxide while adding ice, whereby a precipitate formed which crystallized upon being stirred with ether, yielding 2-(4-amino-3,5-dibromo-phenyl-imino)-imidazolidine base, m.p. 203°–205° C.

The base was dissolved in a little methanol, the solution was acidified with ethereal hydrochloric acid until acid to Congo red, and ether was added. The precipitate formed thereby was collected and dried, yielding 3.20 gm (13.3% of theory) of the hydrochloride, m.p. 234°–236° C., $R_f$-value 0.4 in mobile phase 50 parts benzene, 40 parts dioxane, 5 parts ethanol, 5 parts concentrated ammonium hydroxide. Carrier: silicagel; visualization: ultraviolet light and potassium iodoplatinate.

EXAMPLE 9

2-(3-Methylmercapto-phenylimino)-imidazolidine hydrobromide by method A

A mixture of 42.50 gm of 2-(3-methylmercapto-phenyl)-S-methyl-isothiouronium iodide (0.125 mol), 125 ml of methanol and 12.5 ml of ethylenediamine was refluxed for 6 hours. Thereafter, the reaction mixture was evaporated to dryness, the oily residue was dissolved in a little methanol, and the solution was made alkaline with aqueous 50% potassium hydroxide while adding ice. The precipitate formed thereby, the free 2-(3-methylmercapto-phenylimino)-imidazolidine base, was dissolved in 2 N hydrochloric acid, the solution was extracted with ether, and the ethereal extracts were discarded. The aqueous phase was made stepwise alkaline with 2 N sodium hydroxide and was then fractionally extracted with ether. The uniform ethereal extracts were combined, dried with magnesium sulfate and purified with activated charcoal. The organic phase was then made acid to Congo red with 65% hydrobromic acid, whereupon a white amorphous powder separated out which was isolated and dried. Yield: 6 gm (16.7% of theory) of the hydrobromide, m.p. 147°–148° C., $R_f$-value 0.3 in mobile phase 50 parts benzene, 40 parts dioxane, 5 parts ethanol, 5 parts concentrated ammonium hydroxide. Carrier: silicagel; visualization: ultraviolet light and potassium iodoplatinate.

EXAMPLE 10

2-(3,4,5-Trihydroxy-phenylimino)-imidazolidine hydrobromide by method B

A mixture of 8 gm (0.032 mol) of 2-(3,4,5-trimethoxy-phenylimino)-imidazolidine base and 150 ml of 48% of hydrobromic acid was refluxed for 5 hours on an oil bath. Thereafter, the reaction mixture was evaporated in vacuo to half its original volume and allowed to stand overnight in the refrigerator. The amorphous precipitate which had formed was isolated and dried, yielding 7.3 gm (78.6% of theory) of 2-(3,4,5-trihydroxy-phenylimino)-imidazolidine hydrobromide, m.p. 204°–206° C., $R_f$-value 0.3 in mobile phase 75 parts sec.butanol, 15 parts formic acid, 10 parts water. Carrier: silicagel, visualization; potassium iodoplatinate.

The starting compound was prepared by reacting N-(3,4,5-trimethoxy-phenyl)-S-methyl-isothiourea with ethylenediamine mono-p-toluenesulfonate.

EXAMPLE 11

2-(3-Bromo-4-fluoro-phenylimino)-imidazolidine hydrochloride 10.75 gm (0.06 mol) of 2-(4-fluoro-phenylimino)-imidazolidine base were dissolved in 210 ml of chloroform, and the solution was dropwise admixed with bromine at 10° C. while thoroughly stirring. A solid substance precipitated. The mixture was stirred for 30 minutes at 10° C., then suction-filtered, and the filter cake was thoroughly washed with ether and dried, yielding raw 2-(3-bromo-4-fluoro-phenyl-imino)-imidazolidine hydrobromide, m.p. 137°–139° C. The raw hydrobromide was dissolved in water, and the solution was fractionally extracted with ether at gradually increasing pH-values (stepwise alkalization with 2 N sodium hydroxide). The thin layer-chromatographically uniform ether extracts were combined, dried over magnesium sulfate, filtered and acidified with ethereal hydrochloric acid until acid to Congo red. A white substance separated out, which was collected by suction filtration, washed with ether and dried. Yield: 4.12 gm (23.3% of theory) of the hydrochloride, m.p. 182.5° C., $R_f$-value 0.7 in mobile phase 50 parts benzene, 40 parts dioxane, 5 parts concentrated ammonia, 5 parts ethanol. Carrier: silicagel with fluorescent pigment ZS; visualization; ultraviolet light and potassium platinate.

The compounds of the present invention, that is, those embraced by formula I and their non-toxic, pharmacologically acceptable acid addition salts, have useful pharmacodynamic properties. More particularly, they exhibit strong bradycardiac activity in warm-blooded animals, such as rabbits and cats, and are therefore useful for the treatment of coronary disorders.

For pharmaceutical purposes the compounds of the present invention are administered to warm-blooded animals enterally or parenterally as active ingredients in customary dosage unit compositions, that is, compositions in dosage unit form consisting essentially of an inert pharmaceutical carrier and one effective dosage unit of the active ingredient, such as tablets, coated pills, capsules, wafers, powders, solutions, suspensions, emulsions, syrups, suppositories and the like. One effective dosage unit of the compounds according to the present invention is from 0.0016 to 1.33 mgm/kg body weight, preferably 0.0083 to 0.5 mgm/kg body weight.

The following examples illustrate a few pharmaceutical dosage unit compositions comprising a compound of the present invention as an active ingredient and represent the best modes contemplated of putting the invention into practical use. The parts are parts by weight unless otherwise specified.

EXAMPLE 12

Tablets

The tablet composition is compounded from the following ingredients:

| | | |
|---|---:|---|
| 2-(2-Bromo-4,5-dihydroxy-phenylimino)-imidazolidine hydrobromide | 5 | parts |
| Lactose | 65 | parts |
| Corn starch | 130 | parts |
| Sec. calcium phosphate | 40 | parts |
| Soluble starch | 3 | parts |
| Magnesium stearate | 3 | parts |
| Colloidal silicic acid | 4 | parts |
| Total | 250 | parts |

Preparation

The active ingredient is admixed with a portion of all of the excipients, the mixture is moistened with an aqueous solution of the soluble starch, the moist mass is granulated by passing it through a screen, and the granulate is dried. The dry granulate is admixed with the remainder of the excipients, and the composition is compressed into 250 mgm-tablets. Each tablet is an oral dosage unit composition containing 5 mgm of the active ingredient.

EXAMPLE 13

| | | |
|---|---:|---|
| Hypodermic solution | | |
| The solution is compounded from the following ingredients: | | |
| 2-(3-Chloro-4-hydroxy-phenyliminio)-imidazolidine hydrobromide | 1.0 | parts |
| Sodium chloride | 18.0 | parts |
| Distilled water    q.s.ad | 2000.0 | parts by vol. |

Preparation

The active ingredient and the sodium chloride are dissolved in the distilled water, and the solution is filled under aseptic conditions and in an atmosphere of nitrogen into 2 cc-ampules which are subsequently sterilized and sealed. The contents of each ampule are an injectable dosage unit composition containing 1 mgm of the active ingredient.

EXAMPLE 14

Drop solution

The solution is compounded from the following ingredients:

| | | |
|---|---:|---|
| 2-(4-Bromo-2,5-dihydroxy-phenylimino)-imidazolidine hydrobromide | 0.02 | parts |
| Methyl p-hydroxy-benzoate | 0.07 | parts |
| Propyl p-hydroxy-benzoate | 0.03 | parts |
| Demineralized water    q.s.ad | 100.0 | parts by vol |

Preparation

The active ingredient and the p-hydroxy-benzoates are dissolved in the demineralized water. 5 ml (20 drops) of the solution are an oral dosage unit composition containing 1 mgm of the active ingredient.

Any one of the other compounds embraced by formula I or a non-toxic, pharmacologically acceptable acid addition salt thereof may be substituted for the particular active ingredient in Examples 12 through 14. Likewise, the amount of active ingredient in these illustrative examples may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. The method of slowing the heart rate of a warm-blooded animal in need thereof, which comprises enterally or parenterally administering to said animal an effective bradycardiac amount of a compound of the formula

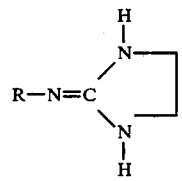

wherein
R is 2-bromo-4,5-dihydroxy-phenyl; 3-chloro-4-hydroxy-phenyl; 4-bromo-2,5-dihydroxy-phenyl; 3,5-dihydroxy-phenyl; 5-chloro-2,4-dihyroxyphenyl; 3-hydroxy-4-methyl-phenyl; 2,6-dibromo-4-hydroxy-methyl-phenyl; 3,5-dibromo-4-aminophenyl; 3-methyl-mercapto-phenyl; 3,4,5-trihydroxy-phenyl; or 3-bromo-4-fluoro-phenyl;
or a non-toxic, pharmacologically acceptable acid addition salt thereof.

* * * * *